United States Patent [19]

Forkner

[11] Patent Number: 4,697,577

[45] Date of Patent: Oct. 6, 1987

[54] SCANNING MICROTELESCOPE FOR SURGICAL APPLICATIONS

[75] Inventor: John F. Forkner, Laguna Beach, Calif.

[73] Assignee: Baxter Travenol Laboratories, Inc., Deerfield, Ill.

[21] Appl. No.: 866,452

[22] Filed: May 22, 1986

[51] Int. Cl.$^4$ ............................................... A61B 1/06
[52] U.S. Cl. ........................................................ 128/6
[58] Field of Search ................................ 128/4, 5, 6, 7

[56] References Cited

U.S. PATENT DOCUMENTS

| | | | |
|---|---|---|---|
| 1,680,491 | 8/1928 | Wappler et al. | 128/6 |
| 1,932,470 | 10/1933 | Lehmann | 128/4 X |
| 2,783,757 | 3/1957 | Scholz | 128/4 |
| 2,927,574 | 3/1960 | Scholz | 128/6 |
| 3,548,808 | 12/1970 | Takahashi | 128/6 |
| 4,398,811 | 8/1983 | Nishioka et al. | 128/7 X |
| 4,576,147 | 3/1986 | Hashiguchi | 128/6 |

Primary Examiner—William H. Grieb
Attorney, Agent, or Firm—Weissenberger & Peterson

[57] ABSTRACT

Adjustment of the field-of-view angle in a surgical microtelescope from the outside of the patient's body is made possible by including in the objective optical system an assembly of mutually movable prisms. The prisms can be moved by a wire running alongside the optical fibers which convey illumination through the tube. In one embodiment, a movable prism pivots with respect to a fixed prism about an axis coincident with the axis of the image as it is transmitted between the prisms; in another embodiment, a partially silvered prism is slidable between two fixed prisms so as to pick up the image from one of them in one position, and the image from the other in the other position. Apparatus in the eyepiece is also disclosed to compensate for the rotation of the image when the pivoting embodiment is used.

7 Claims, 11 Drawing Figures

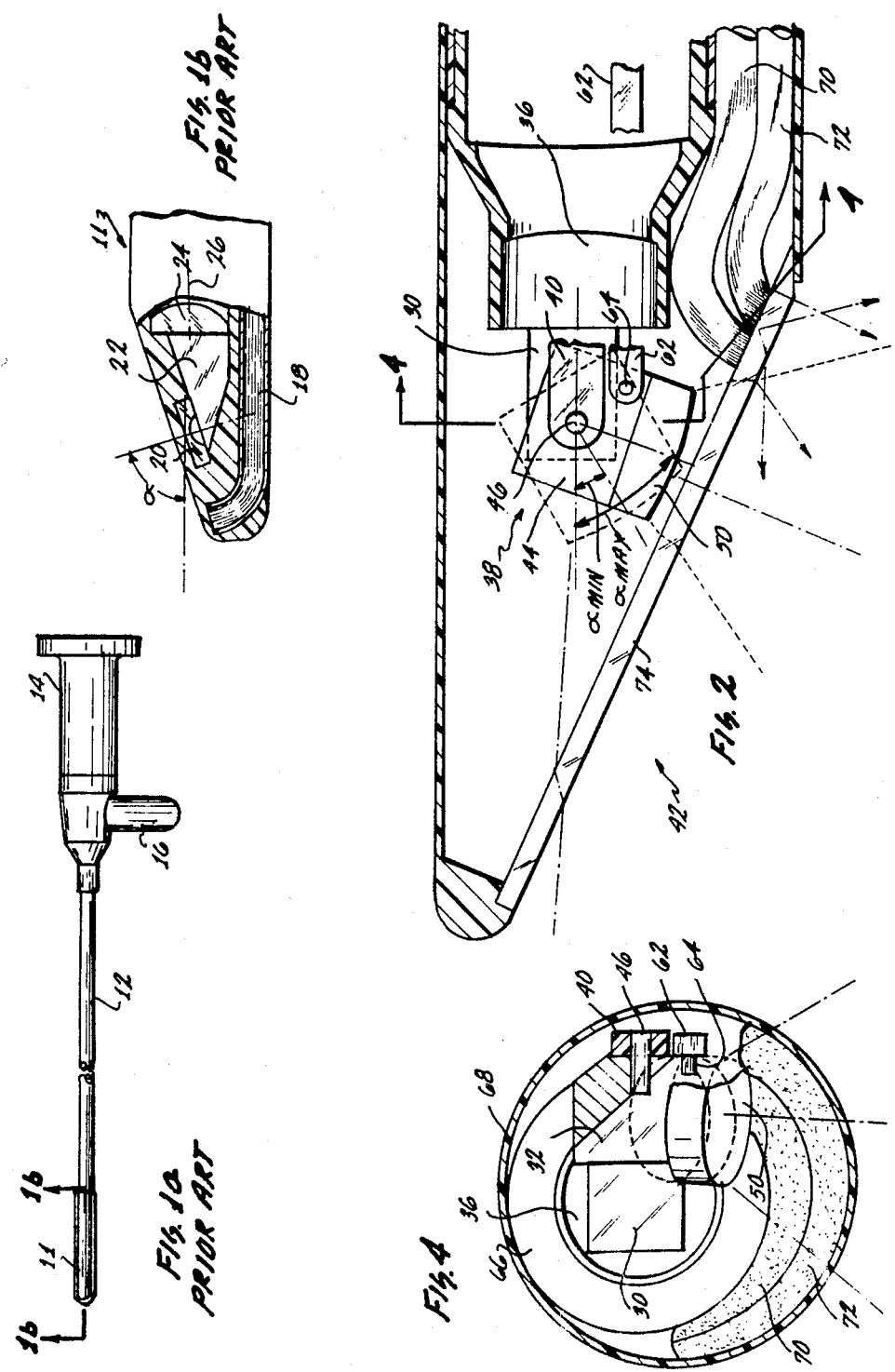

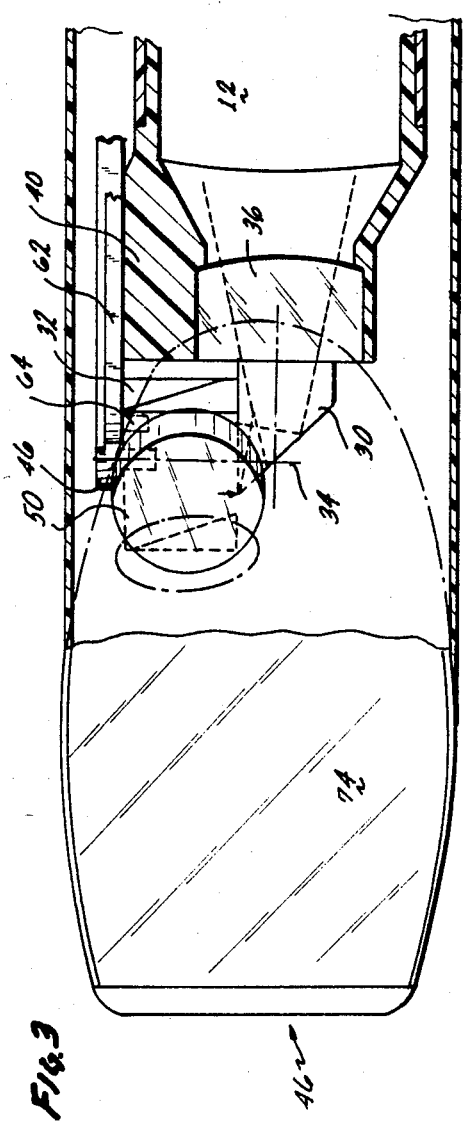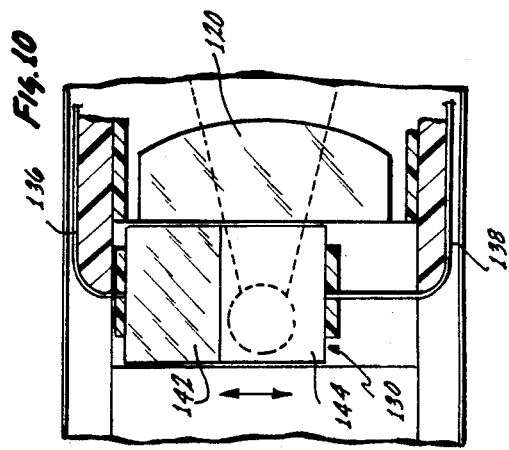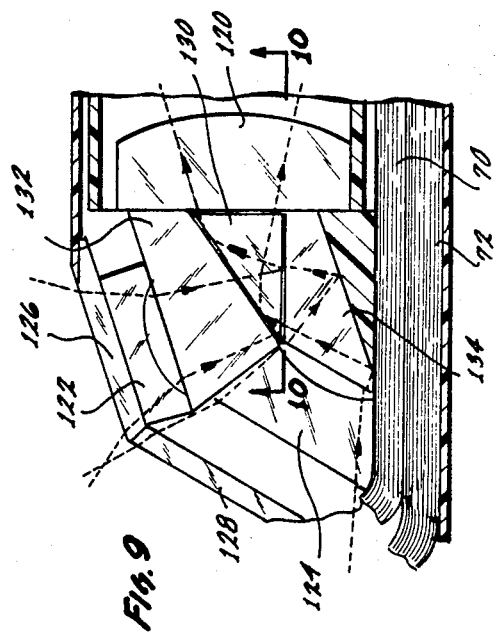

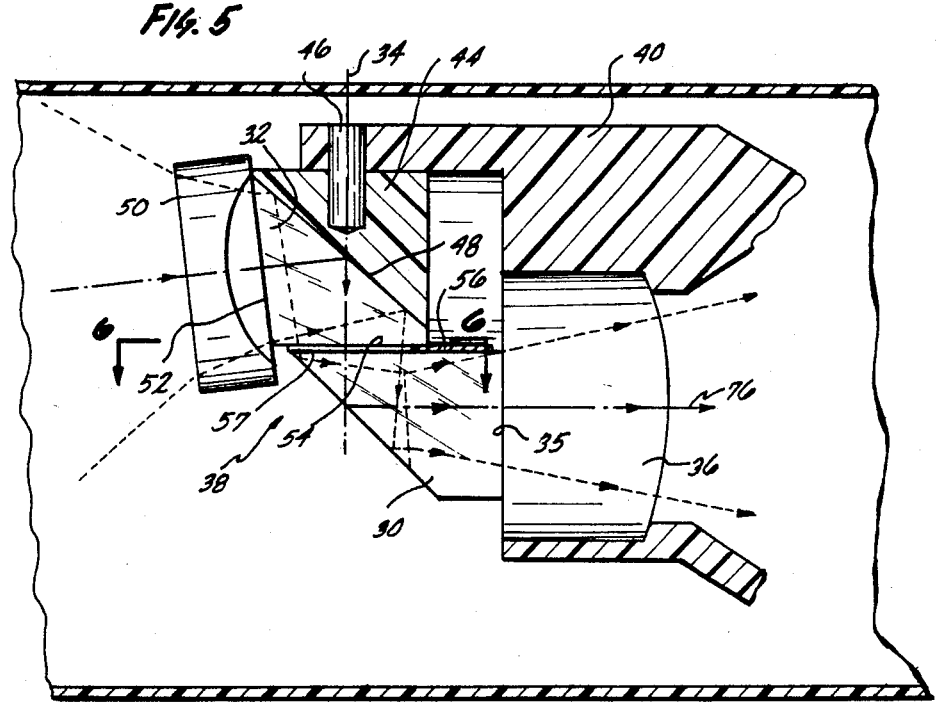
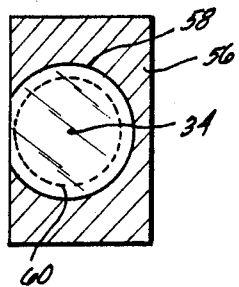

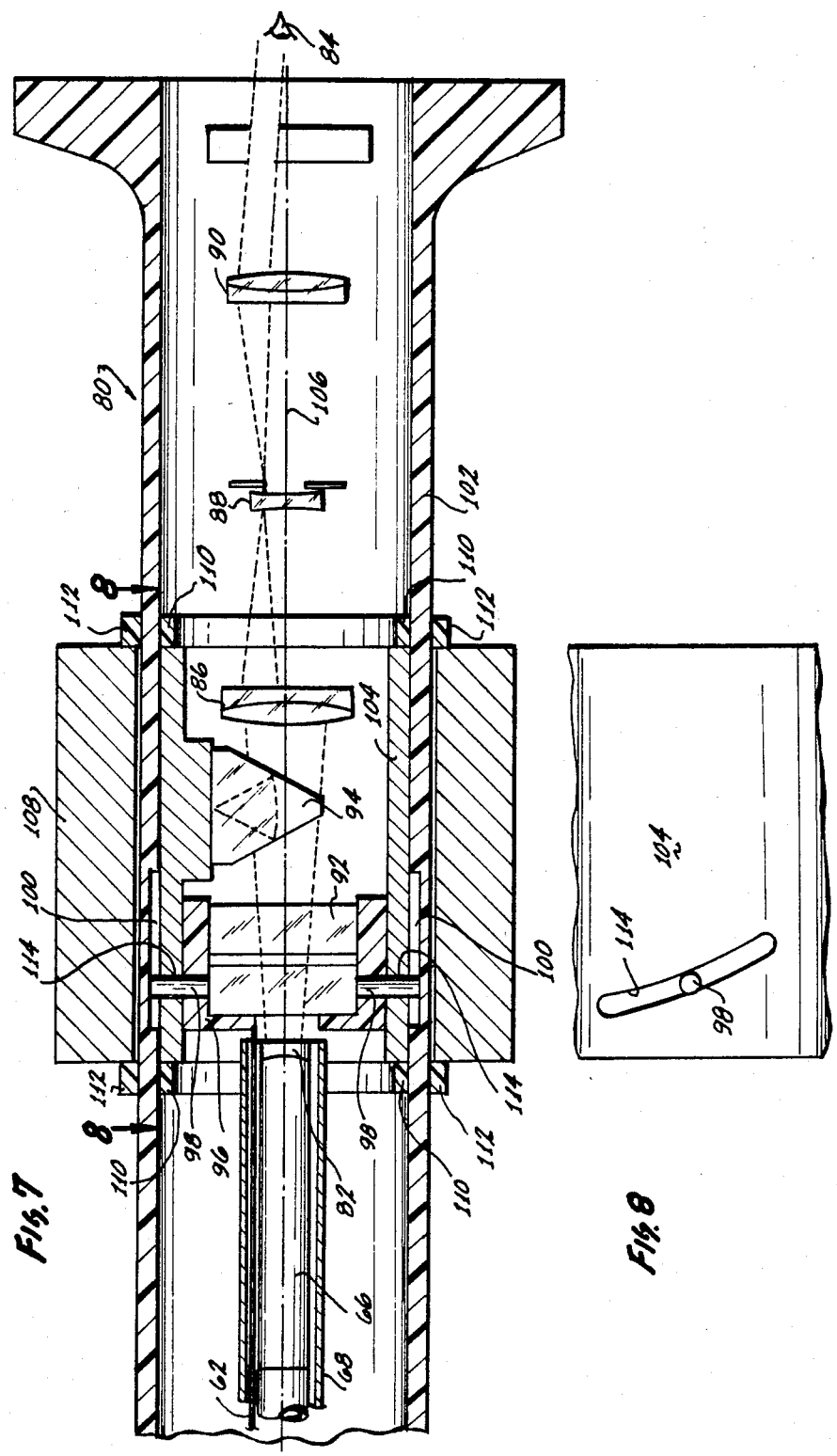

4,697,577

SCANNING MICROTELESCOPE FOR SURGICAL APPLICATIONS

This invention relates to surgical microtelescopes, and more particularly to a device of that type in which the scanning angle can be varied while the device is in place.

BACKGROUND OF THE INVENTION

Scanning microtelescopes such as arthrascopes and cystoscopes are frequently used to examine the interior of the body by threading an optical observation head through a narrow passage in the body. In order to minimize the discomfort to the patient and permit access to a maximum number of body areas the optical observation head must be extremely small, with a diameter of as little as 3 mm. It is obviously very difficult to place any movable objective lens system in such a small enclosure, and even more difficult to actuate it through the long flexible catheter which connects the head to the eyepiece on the outside of the body.

Because of the size constraints and the need for the entire microtelescope to be sterilizable, known expedients such as movable mirrors cannot be used in surgical microtelescopes. Consequently, it has previously been necessary to provide separate instruments for each offset angle (i.e. the angle between the axis of the head and the axis of the field of vision being examined. Thus, if a surgeon wished to observe a body cavity at a 30° viewing angle and then at a 70° viewing angle, the first instrument had to be withdrawn and a second instrument inserted, thereby increasing patient discomfort and the risk of injury.

SUMMARY OF THE INVENTION

The present invention makes it possible to examine a body cavity at several set-off angles, or even at a continuously variable set-off angle, while the instrument is in place, by providing the objective lens system with a split prism whose parts can be moved with respect to one another.

In one embodiment of the invention, the split prism consists of two parts which can be rotated with respect to one another. The rotation can be accomplished by an actuator, such as a stiff wire, which can be brought to the outside of the body through the catheter which connects the head and the eyepiece.

In another embodiment of the invention, a partially mirrored prism can be translated between two fixed prisms so as to interact with one of the fixed prisms in one position, and with the other in another position. This arrangement allows the field of view to be switched between two fixed angles, and it dispenses with the requirement of a stiff actuator.

The use of split prisms makes it possible to confine the motion of the parts within the objective lens system to a very small space without loss of field width or image quality.

It is therefore the object of the invention to provide an objective lens system for surgical microtelescopes which has a variable offset angle.

It is a further object of the invention to provide the foregoing improvement by means of an optical system including a split prism whose parts are relatively movable.

BRIEF DESCRIPTION OF THE DRAWINGS

FIG. 1a is a general side elevation of a prior art device;

FIG. 1b is a partial longitudinal section of the head of the prior art device of FIG. 1a;

FIG. 2 is a vertical longitudinal section of the head of the device of the invention;

FIG. 3 is a plan view, partly in section, of the device of FIG. 2;

FIG. 4 is an end view, partially in section, of the device of FIG. 2;

FIG. 5 is a schematic representation of a portion of the head of FIG. 2 illustrating the optical mechanism involved;

FIG. 6 is a horizontal section along line 6—6 of FIG. 5;

FIG. 7 is a longitudinal vertical section of the eyepiece of the preferred embodiment of the device of this invention;

FIG. 8 is a section along line 8—8 of FIG. 7;

FIG. 9 is a vertical longitudinal section of an alternative embodiment of the invention; and FIG. 10 is a horizontal section along line 10—10 of FIG. 9.

DESCRIPTION OF THE PREFERRED EMBODIMENT

As illustrated in FIGS. 1a and 1b, scanning microtelescopes such as cystoscopes conventionally consist of a head 11 attached to a tube 12 terminating in an eyepiece 14. In use, the head 11 and tube 12 are inserted into the body of the patient, with the eyepiece 14 remaining outside the body of the patient for observation by the physician. A light source 16 is conventionally mounted in the eyepiece 14, and its light is transmitted through optical fibers 18 to the head 11.

Typically, the objective assembly of the head 11 consists of a negative lens 20, a prism 22, and a positive lens 24. The positive lens 24 transmits the image seen by the negative lens 20 to an optical conduit located within the tube 12. The image may be transmitted to the eyepiece 14 through this optical conduit by lens relays, fiber optics, a gradient index relay rod, or any other suitable conventional optical apparatus.

In FIG. 1b, the angle α between the axis 26 of the head 11 and the axis 28 of the field of view of the lens 20 is on the order of 70°. Typically, cystoscopes are manufactured with a view angle of 70° or 30° for the most common purposes.

It should be noted that the typical diameter of the head 11 for surgical microtelescopes is on the order of 3 mm, and that its walls must be thick enough to be sturdy and to be easily sterilizable. Consequently, the components of the objective system must be extremely small and precisely aligned. Also, the field of view of the lens 20 must have a rather wide angle in order to afford the physician a useful view. For these reasons, conventional means such as tiltable mirrors cannot be used to vary the angle α in any given cystoscope, and the instrument has to be removed and another reinserted if the physician desires different view angles—a procedure which is not only cumbersome for the physician, but also uncomfortable for the patient and a potential source of injury.

The present invention makes practical a surgical microtelescope in which the field-of-view angle α can be changed by the physician without removing the instrument, either between two fixed settings or continuously between two limits.

As schematically best illustrated in FIG. 5 and illustrated in place within an observation head in FIGS. 2 through 4, the objective system of a preferred embodiment of this invention is similar to that of the prior art except that the prism 22 of FIG. 1b is replaced by a split prism assembly consisting (in the preferred embodiment) of two prisms 30, 32 which are rotatable with respect to one another about an axis 34.

In the embodiment of FIGS. 2 through 6, the prism 30 is fixedly attached by its face 35 to the positive lens 36 of the objective assembly 38. The lens 36 is in turn fixedly mounted in a bracket 40 anchored in the head 42. A pivot block 44 pivotably supported on a pin 46 of the bracket 40 carries the prism 32 by its major face 48. A negative lens 50 is attached to the minor face 52 of the prism 32. (The negative lens 50 may be omitted in certain applications without departing from the invention.) The other minor face 54 of the prism 32 rests on a thin sheet 56 of Teflon or other lubricous plastic material which covers the face 57 of prism 30 and which is cut out, as shown in FIG. 6, at 58 in such a way as not to obstruct the transmission of the image beam 60 along axis 34 from prism 32 to prism 30.

Referring now to FIG. 2, pivoting movement of the prism 32 about the axis 34 (i.e. the axis of the image beam at the interface between prisms 30 and 32) is accomplished by longitudinally reciprocating the actuating arm 62 which is pivotally attached at 64 to the pivot block 44. The actuating arm 62 may be flat as shown, or it may be a stiff wire or rod whose distal end has been flattened to engage the pin 64, and it may extend alongside the optical conduit 66 through the crescent-shaped portion (FIG. 4) of the catheter 68 which houses the glass fiber bundles 70, 72 of the illumination system described below.

The objective assembly of this invention looks out of the head 42 through a transparent window 74. As best seen in FIG. 2, the field of view of negative lens 50 can easily move between an $\alpha_{max}$ position where $\alpha$ is 70° (solid and dotted lines) to an $\alpha_{min}$ position where $\alpha$ is 30° (dot-dash lines). Inasmuch as the inner portions of the view fields in these positions overlap, it will be seen that by pivoting the prism 32, the physician can visualize the entire range of images from straight ahead of the head 42 to 90° to its side.

Because of the width of the resulting total field of view, it is necessary in the preferred embodiment to provide two illumination fiber bundles 70 and 72. The bundle 70 is attached to the window 74 at such an angle as to illuminate the field of view when $\alpha$ is 70°, while the bundle 72 is attached at such an angle as to illuminate the field of view at $\alpha = 30°$. Between the two, the entire available field of view is illuminated. Alternatively, a single fiber bundle (not shown) may be used in which various individual fibers are attached to the window 74 at various angles.

Returning now to FIG. 5, those versed in optics will note that pivoting prism 32 about the image beam axis 34 will cause the image transmitted into the optical conduit 66 to rotate about axis 76. To compensate for this annoying effect, the eyepiece 80 may be constructed as shown in FIGS. 7 and 8. In FIG. 7, the optical conduit 66 terminates in a lens 82 which allows the eye 84 to observe the image through a telescopic lens system 86, 88, 90. The image is observed through a set of Schmidt prisms 92, 94.

The prism 92 is mounted in a slide block 96 provided with guide pins 98 which engage a pair of longitudinal slots 100 formed in the barrel 102 of the eyepiece 80. The slots 100 allow the slide block 96 to move in an axial direction within the barrel 102 but prevent it from rotating. The prism 94, on the other hand, is mounted on the inside of a hollow cylindrical support 104 of magnetic material which can be rotated about the axis 106 of the barrel 102 by an annular rotatable magnet 108. The support 104 and magnet 108 are restrained against axial movement by retaining rings 110 and 112, respectively.

As shown in FIG. 8, the cylindrical support 104 is provided with slots 114 traversed by the guide pins 98 of slide block 96. Thus, when the support 104 (and with it the prism 94) is rotated about the axis 106, the slide block 96 is reciprocated in the direction of the axis 106. As shown in FIG. 7, the actuating arm or wire 62 is secured to slide block 96 so as to pivot the prism 32 in the head 42 (FIG. 2) as the slide block 96 reciprocates.

With the proper configuration of slot 114, the mutual rotation of prisms 92 and 94 as the slide block 96 reciprocates can be made to compensate exactly for the rotation of the image caused by the pivoting of prism 32 as a result of the reciprocation of slide block 96. Thus, the image seen by the observer 84 remains upright as the angle $\alpha$ of the field-of-view axis in the head 42 changes.

An alternative embodiment of the invention in which the field of view is switchable between two fixed positions is shown in FIGS. 9 and 10. In that embodiment, the prism system interposed between the positive lens 120 and the negative lenses 122, 124 (which look, respectively, through the windows 126, 128) consists of three prisms 130, 132, 134, of which only two are active at any given time. (As mentioned before, the negative lenses 122, 124 may be omitted in certain applications.)

As best shown in FIG. 10, the central prism 130 is transversely reciprocable by alternately pulling the flexible wires 136, 138. The minor face 140 of prism 130 is silvered on half of its area (142) and clear on the other half (144). In the position of prism 130 shown in FIG. 10, the image seen by lens 124 through window 128 (at an $\alpha_{min}$ angle of 30°) is transmitted through prisms 134 and 130, as shown in dotted lines, to lens 120. If the prism 130 is moved downward in FIG. 10, the mirrored surface 142 blocks the image from window 128 and instead reflects the image from window 126 (at the $\alpha_{max}$ angle of 70°) through lens 122 and prism 132 into lens 120.

It will be noted that in this alternative embodiment, the two images are neither rotated nor inverted with respect to one another, so that no eyepiece compensation is needed.

I claim:

1. A surgical microtelescope comprising:
   (a) an elongated, sterilizable observation head;
   (b) an eyepiece;
   (c) elongated optical conduit means connecting said head and eyepiece for transmitting an image from said head to said eyepiece;
   (d) said head having mounted therein an objective optical system including a plurality of prisms movable relative to one another; and
   (e) actuating means connected to one of said prisms and extending between said head and the eyepiece end of said conduit means for imparting relative movement to said prisms from said eyepiece end of said conduit means;

(f) said relative movement of said prisms being such as to vary the angle between the axis of the field of view of said objective optical system and the axis of said head.

2. The apparatus of claim 1, in which:
(i) said objective optical system includes a lens interposed between a pair of prisms and said conduit means, said lens being substantially coaxial with said conduit means;
(ii) one of said prisms being fixed and having a first side positioned adjacent said lens;
(iii) the other said prisms having a first side exposed to the field of view of said objective optical system;
(iv) a second side of said one prism being parallel to a second side of said other prism; and
(v) said other prism being pivotable about an axis perpendicular to said parallel sides and extending substantially through the center thereof.

3. The apparatus of claim 1, in which said relative movement is a pivoting movement about an axis coincident with the axis of the path along which said image is transmitted between said prisms.

4. The apparatus of claim 1, in which:
(i) said objective system includes a lens adjacent said optical conduit and at least three prisms, one of said prisms being movable with respect to each of the other prisms;
(ii) said movable prism having a partially mirrored surface so disposed that in one position of said movable prism, a first image is transmitted through one of said other prisms and said movable prism to said lens, and that in the other position of said movable lens, a second image is transmitted through the other of said other prisms and said movable prism to said lens.

5. The apparatus of claim 4, in which said other prisms are fixed, and said movable prism is slidably movable between them.

6. The apparatus of claim 2, further comprising:
(g) means in said eyepiece for moving said actuating means so as to pivot said other prism;
(h) a pair of relatively rotatable prisms in said eyepiece; and
(j) means interconnecting said relatively rotatable prisms and said means for moving said actuating means so as to relatively rotate said last-named prisms conjointly with the movement of said actuating means in such a manner as to compensate for the rotation of said image when said other prism is pivoted by said actuating means.

7. The apparatus of claim 6, in which last-named means include:
(i) a slide block attached to said actuating means and carrying one of said relatively rotatable prisms; and
(ii) a rotatable support carrying the other of said relatively rotatable prisms;
(iii) said slide block and support being so interconnected that rotation of said support causes said slide block to move longitudinally of said eyepiece without rotation and thereby to operate said actuating means.

* * * * *